United States Patent [19]
Uchino et al.

[11] Patent Number: 5,955,069
[45] Date of Patent: Sep. 21, 1999

[54] USE OF CANINE INTERFERON-γ(IFN-γ) TO TREAT NON-ATOPIC DERMATITIS

[75] Inventors: Tomiya Uchino, Tokyo; Katsushige Yamada, Aichi; Fumiyoshi Okano, Nagoya; Masahiro Satoh, Kamakura; Isao Kawakami, Tokyo, all of Japan

[73] Assignee: Toray Industries, Inc., Chiba, Japan

[21] Appl. No.: 09/001,944

[22] Filed: Dec. 31, 1997

[30] Foreign Application Priority Data

Mar. 6, 1997 [JP] Japan ................................. 9-051612

[51] Int. Cl.$^6$ ............................ A61K 38/21; C12N 15/23
[52] U.S. Cl. ........................................................ 424/85.5
[58] Field of Search ........................ 424/85.5; 435/69.51

[56] References Cited

PUBLICATIONS

Ijzermans et al., *Immunobiology*, 179, 456–473 (1989).
Himmler et al., *J. Interferon Research*, 7, 173–183 (1987).
Devos et al., *J. Interferon Research*, 12, 95–102 (1992).
Hanifin et al., *J. Am. Acad. Dermatol.*, 28, 189–197 (1993).
Reinhold et al., *Lancet*, 335, 1282 (1990).
Reinhold et al., *J. Am Acad. Dermatol.*, 29, 58–63 (1993).
Nishioka et al., *J. Dermatol.*, 22, 181–185 (1995).
Williams, *Br. J. Dermatol.*, 131, 397–405 (1994).
Sampson et al., *J. Allergy Clin. Immunol.*, 81, 635–645 (1988).
H. Tagami, *Jpn. J. Dermatol.*, 106, 955–964 (1996).
Horiuchi et al., *Agic. Biol. Chem.*, 51, 1573–1580 (1987).
Zucker, K., et al. (1993) *J. Interferon Res.* 13 (2): 91–97.
Drug Data Report database, Dialog accession No. 00168624, accessed Sep. 21, 1998.

*Primary Examiner*—David L. Fitzgerald
*Attorney, Agent, or Firm*—Birch, Stewart, Kolasch & Birch, LLP

[57] ABSTRACT

Methods for treating intractable dermatitis in dogs are described. The methods involve the administration by injection of formulations comprising canine interferon-γ and, optionally, other agents. The canine IFN-γ may be produced in recombinant expression systems such as *E. coli* or *B. mori*.

17 Claims, No Drawings the canine IFN-γ gene has been transduced into a eukaryotic cell such as silkworms (*Bombyx mori*), insect cells, or animal cells, canine IFN-γ can be obtained from the cells or culture supernatants. Characteristics of canine IFN-γ produced by using such cells have been described in detail in Japanese patent applications (Hei 4-63595 and Hei 4-63596).

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 498 base pairs
      (B) TYPE: nucleic acid
      (C) STRANDEDNESS: Not Relevant
      (D) TOPOLOGY: Not Relevant (ii) MOLECULE TYPE: cDNA (iii) HYPOTHETICAL: NO (iv) ANTI-SENSE: NO (ix) FEATURE:
      (A) NAME/KEY: sig_peptide
      (B) LOCATION: 1..72

(ix) FEATURE:
      (A) NAME/KEY: mat_peptide
      (B) LOCATION: 73..498

(ix) FEATURE:
      (A) NAME/KEY: CDS
      (B) LOCATION: 1..498

(xi) SEQUENCE DESCRIPTION: SEQ ID NO:1:

```
ATG AAT TAT ACA AGC TAT ATC TTA GCT TTT CAG CTT TGC GTG ATT TTG        48
Met Asn Tyr Thr Ser Tyr Ile Leu Ala Phe Gln Leu Cys Val Ile Leu
-24             -20             -15             -10

TGT TCT TCT GGC TGT AAC TGT CAG GCC ATG TTT TTT AAA GAA ATA GAA        96
Cys Ser Ser Gly Cys Asn Cys Gln Ala Met Phe Phe Lys Glu Ile Glu
            -5                   1               5

AAC CTA AAG GAA TAT TTT AAT GCA AGT AAT CCA GAT GTA TCG GAC GGT       144
Asn Leu Lys Glu Tyr Phe Asn Ala Ser Asn Pro Asp Val Ser Asp Gly
        10              15              20

GGG TCT CTT TTC GTA GAT ATT TTG AAG AAA TGG AGA GAG GAG AGT GAC       192
Gly Ser Leu Phe Val Asp Ile Leu Lys Lys Trp Arg Glu Glu Ser Asp
25              30              35              40

AAA ACA ATC ATT CAG AGC CAA ATT GTC TCT TTC TAC TTG AAA CTG TTT       240
Lys Thr Ile Ile Gln Ser Gln Ile Val Ser Phe Tyr Leu Lys Leu Phe
                45              50              55

GAC AAC TTT AAA GAT AAC CAG ATC ATT CAA AGG AGC ATG GAT ACC ATC       288
Asp Asn Phe Lys Asp Asn Gln Ile Ile Gln Arg Ser Met Asp Thr Ile
            60              65              70

AAG GAA GAC ATG CTT GGC AAG TTC TTA AAT AGC AGC ACC AGT AAG AGG       336
Lys Glu Asp Met Leu Gly Lys Phe Leu Asn Ser Ser Thr Ser Lys Arg
        75              80              85

GAG GAC TTC CTT AAG CTG ATT CAA ATT CCT GTC AAC GAT CTG CAG GTC       384
Glu Asp Phe Leu Lys Leu Ile Gln Ile Pro Val Asn Asp Leu Gln Val
    90              95              100

CAG CGC AAG GCG ATA AAT GAA CTC ATC AAA GTG ATG AAT GAT CTC TCA       432
Gln Arg Lys Ala Ile Asn Glu Leu Ile Lys Val Met Asn Asp Leu Ser
105             110             115             120

CCA AGA TCC AAC CTA AGG AAG CGG AAA AGG AGT CAG AAT CTG TTT CGA       480
```

```
Pro Arg Ser Asn Leu Arg Lys Arg Lys Arg Ser Gln Asn Leu Phe Arg
            125                 130                 135

GGC CGC AGA GCA TCG AAA                                                    498
Gly Arg Arg Ala Ser Lys
            140
```

(2) INFORMATION FOR SEQ ID NO:2:

(i) SEQUENCE CHARACTERISTICS:
        (A) LENGTH: 166 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asn Tyr Thr Ser Tyr Ile Leu Ala Phe Gln Leu Cys Val Ile Leu
-24             -20                 -15                 -10

Cys Ser Ser Gly Cys Asn Cys Gln Ala Met Phe Phe Lys Glu Ile Glu
            -5                   1                   5

Asn Leu Lys Glu Tyr Phe Asn Ala Ser Asn Pro Asp Val Ser Asp Gly
        10                  15                  20

Gly Ser Leu Phe Val Asp Ile Leu Lys Lys Trp Arg Glu Glu Ser Asp
 25                  30                  35                  40

Lys Thr Ile Ile Gln Ser Gln Ile Val Ser Phe Tyr Leu Lys Leu Phe
                45                  50                  55

Asp Asn Phe Lys Asp Asn Gln Ile Ile Gln Arg Ser Met Asp Thr Ile
            60                  65                  70

Lys Glu Asp Met Leu Gly Lys Phe Leu Asn Ser Ser Thr Ser Lys Arg
                75                  80                  85

Glu Asp Phe Leu Lys Leu Ile Gln Ile Pro Val Asn Asp Leu Gln Val
            90                  95                  100

Gln Arg Lys Ala Ile Asn Glu Leu Ile Lys Val Met Asn Asp Leu Ser
105                 110                 115                 120

Pro Arg Ser Asn Leu Arg Lys Arg Lys Arg Ser Gln Asn Leu Phe Arg
            125                 130                 135

Gly Arg Arg Ala Ser Lys
            140
```

(2) INFORMATION FOR SEQ ID NO:3:

(i) SEQUENCE CHARACTERISTICS:
        (A) LENGTH: 498 base pairs
        (B) TYPE: nucleic acid
        (C) STRANDEDNESS: Not Relevant
        (D) TOPOLOGY: Not Relevant (ii) MOLECULE TYPE: cDNA (iii) HYPOTHETICAL: NO (ix) FEATURE:
        (A) NAME/KEY: sig_peptide
        (B) LOCATION: 1..72

(ix) FEATURE:
        (A) NAME/KEY: mat_peptide
        (B) LOCATION: 73..498

(ix) FEATURE:
        (A) NAME/KEY: CDS
        (B) LOCATION: 1..498

(xi) SEQUENCE DESCRIPTION: SEQ ID NO:3:

```
ATG AAT TAT ACA AGC TAT ATC TTA GCT TTT CAG CTT TGC GTG ATT TTG        48
```

```
Met Asn Tyr Thr Ser Tyr Ile Leu Ala Phe Gln Leu Cys Val Ile Leu
-24             -20                 -15                 -10

TGT TCT TCT GGC TGT AAC TGT CAG GCC ATG TTT TTT AAA GAA ATA GAA       96
Cys Ser Ser Gly Cys Asn Cys Gln Ala Met Phe Phe Lys Glu Ile Glu
            -5                   1               5

AAC CTA AAG GAA TAT TTT AAT GCA AGT AAT CCA GAT GTA TCG GAC GGT      144
Asn Leu Lys Glu Tyr Phe Asn Ala Ser Asn Pro Asp Val Ser Asp Gly
         10              15              20

GGG TCT CTT TTC GTA GAT ATT TTG AAG AAA TGG AGA GAG GAG AGT GAC      192
Gly Ser Leu Phe Val Asp Ile Leu Lys Lys Trp Arg Glu Glu Ser Asp
 25              30              35              40

AAA ACA ATC ATT CAG AGC CAA ATT GTC TCT TTC TAC TTG AAA CTG TTT      240
Lys Thr Ile Ile Gln Ser Gln Ile Val Ser Phe Tyr Leu Lys Leu Phe
                 45              50              55

GAC AAC TTT AAA GAT AAC CAG ATC ATT CAA AGG AGC ATG GAT ACC ATC      288
Asp Asn Phe Lys Asp Asn Gln Ile Ile Gln Arg Ser Met Asp Thr Ile
             60              65              70

AAG GAA GAC ATG CTT GGC AAG TTC TTA CAG AGC AGC ACC AGT AAG AGG      336
Lys Glu Asp Met Leu Gly Lys Phe Leu Gln Ser Ser Thr Ser Lys Arg
         75              80              85

GAG GAC TTC CTT AAG CTG ATT CAA ATT CCT GTC AAC GAT CTG CAG GTC      384
Glu Asp Phe Leu Lys Leu Ile Gln Ile Pro Val Asn Asp Leu Gln Val
 90              95             100

CAG CGC AAG GCG ATA AAT GAA CTC ATC AAA GTG ATG AAT GAT CTC TCA      432
Gln Arg Lys Ala Ile Asn Glu Leu Ile Lys Val Met Asn Asp Leu Ser
105             110             115             120

CCA AGA TCC AAC CTA AGG AAG CGG AAA AGG AGT CAG AAT CTG TTT CGA      480
Pro Arg Ser Asn Leu Arg Lys Arg Lys Arg Ser Gln Asn Leu Phe Arg
            125             130             135

GGC CGC AGA GCA TCG AAA                                              498
Gly Arg Arg Ala Ser Lys
            140
```

(2) INFORMATION FOR SEQ ID NO:4:

(i) SEQUENCE CHARACTERISTICS:
        (A) LENGTH: 166 amino acids
        (B) TYPE: amino acid
        (D) TOPOLOGY: linear (ii) MOLECULE TYPE: protein (xi) SEQUENCE DESCRIPTION: SEQ ID NO:4:

```
Met Asn Tyr Thr Ser Tyr Ile Leu Ala Phe Gln Leu Cys Val Ile Leu
-24             -20                 -15                 -10

Cys Ser Ser Gly Cys Asn Cys Gln Ala Met Phe Phe Lys Glu Ile Glu
            -5                   1               5

Asn Leu Lys Glu Tyr Phe Asn Ala Ser Asn Pro Asp Val Ser Asp Gly
         10              15              20

Gly Ser Leu Phe Val Asp Ile Leu Lys Lys Trp Arg Glu Glu Ser Asp
 25              30              35              40

Lys Thr Ile Ile Gln Ser Gln Ile Val Ser Phe Tyr Leu Lys Leu Phe
                 45              50              55

Asp Asn Phe Lys Asp Asn Gln Ile Ile Gln Arg Ser Met Asp Thr Ile
             60              65              70

Lys Glu Asp Met Leu Gly Lys Phe Leu Gln Ser Ser Thr Ser Lys Arg
         75              80              85

Glu Asp Phe Leu Lys Leu Ile Gln Ile Pro Val Asn Asp Leu Gln Val
 90              95             100

Gln Arg Lys Ala Ile Asn Glu Leu Ile Lys Val Met Asn Asp Leu Ser
```

```
    105                 110                 115                 120
Pro Arg Ser Asn Leu Arg Lys Arg Lys Arg Ser Gln Asn Leu Phe Arg
                125                 130                 135

Gly Arg Arg Ala Ser Lys
            140

(2) INFORMATION FOR SEQ ID NO:5:

(i) SEQUENCE CHARACTERISTICS:
        (A) LENGTH: 498 base pairs
        (B) TYPE: nucleic acid
        (C) STRANDEDNESS: Not Relevant
        (D) TOPOLOGY: Not Relevant (ii) MOLECULE TYPE: cDNA (iii) HYPOTHETICAL: NO (ix) FEATURE:
        (A) NAME/KEY: sig_peptide
        (B) LOCATION: 1..72

(ix) FEATURE:
        (A) NAME/KEY: mat_peptide
        (B) LOCATION: 73..498

(ix) FEATURE:
        (A) NAME/KEY: CDS
        (B) LOCATION: 1..498

(xi) SEQUENCE DESCRIPTION: SEQ ID NO:5:

ATG AAT TAT ACA AGC TAT ATC TTA GCT TTT CAG CTT TGC GTG ATT TTG         48
Met Asn Tyr Thr Ser Tyr Ile Leu Ala Phe Gln Leu Cys Val Ile Leu
-24                 -20                 -15                 -10

TGT TCT TCT GGC TGT AAC TGT CAG GCC ATG TTT TTT AAA GAA ATA GAA         96
Cys Ser Ser Gly Cys Asn Cys Gln Ala Met Phe Phe Lys Glu Ile Glu
            -5                   1                   5

AAC CTA AAG GAA TAT TTT CAG GCA AGT AAT CCA GAT GTA TCG GAC GGT        144
Asn Leu Lys Glu Tyr Phe Gln Ala Ser Asn Pro Asp Val Ser Asp Gly
        10                  15                  20

GGG TCT CTT TTC GTA GAT ATT TTG AAG AAA TGG AGA GAG GAG AGT GAC        192
Gly Ser Leu Phe Val Asp Ile Leu Lys Lys Trp Arg Glu Glu Ser Asp
 25                  30                  35                  40

AAA ACA ATC ATT CAG AGC CAA ATT GTC TCT TTC TAC TTG AAA CTG TTT        240
Lys Thr Ile Ile Gln Ser Gln Ile Val Ser Phe Tyr Leu Lys Leu Phe
                45                  50                  55

GAC AAC TTT AAA GAT AAC CAG ATC ATT CAA AGG AGC ATG GAT ACC ATC        288
Asp Asn Phe Lys Asp Asn Gln Ile Ile Gln Arg Ser Met Asp Thr Ile
             60                  65                  70

AAG GAA GAC ATG CTT GGC AAG TTC TTA AAT AGC AGC ACC AGT AAG AGG        336
Lys Glu Asp Met Leu Gly Lys Phe Leu Asn Ser Ser Thr Ser Lys Arg
         75                  80                  85

GAG GAC TTC CTT AAG CTG ATT CAA ATT CCT GTC AAC GAT CTG CAG GTC        384
Glu Asp Phe Leu Lys Leu Ile Gln Ile Pro Val Asn Asp Leu Gln Val
     90                  95                 100

CAG CGC AAG GCG ATA AAT GAA CTC ATC AAA GTG ATG AAT GAT CTC TCA        432
Gln Arg Lys Ala Ile Asn Glu Leu Ile Lys Val Met Asn Asp Leu Ser
105                 110                 115                 120

CCA AGA TCC AAC CTA AGG AAG CGG AAA AGG AGT CAG AAT CTG TTT CGA        480
Pro Arg Ser Asn Leu Arg Lys Arg Lys Arg Ser Gln Asn Leu Phe Arg
                125                 130                 135

GGC CGC AGA GCA TCG AAA                                                 498
Gly Arg Arg Ala Ser Lys
            140
```

(2) INFORMATION FOR SEQ ID NO:6:

(i) SEQUENCE CHARACTERISTICS:
        (A) LENGTH: 166 amino acids
        (B) TYPE: amino acid
        (D) TOPOLOGY: linear (ii) MOLECULE TYPE: protein (xi) SEQUENCE DESCRIPTION: SEQ ID NO:6:

```
Met Asn Tyr Thr Ser Tyr Ile Leu Ala Phe Gln Leu Cys Val Ile Leu
-24             -20             -15             -10

Cys Ser Ser Gly Cys Asn Cys Gln Ala Met Phe Phe Lys Glu Ile Glu
            -5              1               5

Asn Leu Lys Glu Tyr Phe Gln Ala Ser Asn Pro Asp Val Ser Asp Gly
        10              15              20

Gly Ser Leu Phe Val Asp Ile Leu Lys Lys Trp Arg Glu Glu Ser Asp
25              30              35              40

Lys Thr Ile Ile Gln Ser Gln Ile Val Ser Phe Tyr Leu Lys Leu Phe
                45              50              55

Asp Asn Phe Lys Asp Asn Gln Ile Ile Gln Arg Ser Met Asp Thr Ile
            60              65              70

Lys Glu Asp Met Leu Gly Lys Phe Leu Asn Ser Ser Thr Ser Lys Arg
        75              80              85

Glu Asp Phe Leu Lys Leu Ile Gln Ile Pro Val Asn Asp Leu Gln Val
        90              95              100

Gln Arg Lys Ala Ile Asn Glu Leu Ile Lys Val Met Asn Asp Leu Ser
105             110             115             120

Pro Arg Ser Asn Leu Arg Lys Arg Lys Arg Ser Gln Asn Leu Phe Arg
                125             130             135

Gly Arg Arg Ala Ser Lys
                140
```

(2) INFORMATION FOR SEQ ID NO:7:

(i) SEQUENCE CHARACTERISTICS:
        (A) LENGTH: 498 base pairs
        (B) TYPE: nucleic acid
        (C) STRANDEDNESS: Not Relevant
        (D) TOPOLOGY: Not Relevant (ii) MOLECULE TYPE: cDNA (iii) HYPOTHETICAL: NO (ix) FEATURE:
        (A) NAME/KEY: sig_peptide
        (B) LOCATION: 1..72

(ix) FEATURE:
        (A) NAME/KEY: mat_peptide
        (B) LOCATION: 73..498

(ix) FEATURE:
        (A) NAME/KEY: CDS
        (B) LOCATION: 1..498

(xi) SEQUENCE DESCRIPTION: SEQ ID NO:7:

```
ATG AAT TAT ACA AGC TAT ATC TTA GCT TTT CAG CTT TGC GTG ATT TTG        48
Met Asn Tyr Thr Ser Tyr Ile Leu Ala Phe Gln Leu Cys Val Ile Leu
-24             -20             -15             -10

TGT TCT TCT GGC TGT AAC TGT CAG GCC ATG TTT TTT AAA GAA ATA GAA        96
Cys Ser Ser Gly Cys Asn Cys Gln Ala Met Phe Phe Lys Glu Ile Glu
            -5              1               5

AAC CTA AAG GAA TAT TTT CAG GCA AGT AAT CCA GAT GTA TCG GAC GGT       144
```

```
Asn Leu Lys Glu Tyr Phe Gln Ala Ser Asn Pro Asp Val Ser Asp Gly
    10              15                  20

GGG TCT CTT TTC GTA GAT ATT TTG AAG AAA TGG AGA GAG GAG AGT GAC        192
Gly Ser Leu Phe Val Asp Ile Leu Lys Lys Trp Arg Glu Glu Ser Asp
 25              30                  35                  40

AAA ACA ATC ATT CAG AGC CAA ATT GTC TCT TTC TAC TTG AAA CTG TTT        240
Lys Thr Ile Ile Gln Ser Gln Ile Val Ser Phe Tyr Leu Lys Leu Phe
                 45                  50                  55

GAC AAC TTT AAA GAT AAC CAG ATC ATT CAA AGG AGC ATG GAT ACC ATC        288
Asp Asn Phe Lys Asp Asn Gln Ile Ile Gln Arg Ser Met Asp Thr Ile
             60                  65                  70

AAG GAA GAC ATG CTT GGC AAG TTC TTA CAG AGC AGC ACC AGT AAG AGG        336
Lys Glu Asp Met Leu Gly Lys Phe Leu Gln Ser Ser Thr Ser Lys Arg
         75                  80                  85

GAG GAC TTC CTT AAG CTG ATT CAA ATT CCT GTC AAC GAT CTG CAG GTC        384
Glu Asp Phe Leu Lys Leu Ile Gln Ile Pro Val Asn Asp Leu Gln Val
     90                  95                 100

CAG CGC AAG GCG ATA AAT GAA CTC ATC AAA GTG ATG AAT GAT CTC TCA        432
Gln Arg Lys Ala Ile Asn Glu Leu Ile Lys Val Met Asn Asp Leu Ser
105             110                 115                 120

CCA AGA TCC AAC CTA AGG AAG CGG AAA AGG AGT CAG AAT CTG TTT CGA        480
Pro Arg Ser Asn Leu Arg Lys Arg Lys Arg Ser Gln Asn Leu Phe Arg
                125                 130                 135

GGC CGC AGA GCA TCG AAA                                                498
Gly Arg Arg Ala Ser Lys
            140

(2) INFORMATION FOR SEQ ID NO:8:

(i) SEQUENCE CHARACTERISTICS:
        (A) LENGTH: 166 amino acids
        (B) TYPE: amino acid
        (D) TOPOLOGY: linear (ii) MOLECULE TYPE: protein (xi) SEQUENCE DESCRIPTION: SEQ ID NO:8:

Met Asn Tyr Thr Ser Tyr Ile Leu Ala Phe Gln Leu Cys Val Ile Leu
-24             -20                 -15                 -10

Cys Ser Ser Gly Cys Asn Cys Gln Ala Met Phe Phe Lys Glu Ile Glu
            -5                   1                   5

Asn Leu Lys Glu Tyr Phe Gln Ala Ser Asn Pro Asp Val Ser Asp Gly
    10              15                  20

Gly Ser Leu Phe Val Asp Ile Leu Lys Lys Trp Arg Glu Glu Ser Asp
 25              30                  35                  40

Lys Thr Ile Ile Gln Ser Gln Ile Val Ser Phe Tyr Leu Lys Leu Phe
                 45                  50                  55

Asp Asn Phe Lys Asp Asn Gln Ile Ile Gln Arg Ser Met Asp Thr Ile
             60                  65                  70

Lys Glu Asp Met Leu Gly Lys Phe Leu Gln Ser Ser Thr Ser Lys Arg
         75                  80                  85

Glu Asp Phe Leu Lys Leu Ile Gln Ile Pro Val Asn Asp Leu Gln Val
     90                  95                 100

Gln Arg Lys Ala Ile Asn Glu Leu Ile Lys Val Met Asn Asp Leu Ser
105             110                 115                 120

Pro Arg Ser Asn Leu Arg Lys Arg Lys Arg Ser Gln Asn Leu Phe Arg
                125                 130                 135

Gly Arg Arg Ala Ser Lys
            140
```

(2) INFORMATION FOR SEQ ID NO:9:

(i) SEQUENCE CHARACTERISTICS:
        (A) LENGTH: 435 base pairs
        (B) TYPE: nucleic acid
        (C) STRANDEDNESS: Not Relevant
        (D) TOPOLOGY: Not Relevant (ii) MOLECULE TYPE: cDNA (iii) HYPOTHETICAL: NO (ix) FEATURE:
        (A) NAME/KEY: mat_peptide
        (B) LOCATION: 1..435

(ix) FEATURE:
        (A) NAME/KEY: CDS
        (B) LOCATION: 1..435

(xi) SEQUENCE DESCRIPTION: SEQ ID NO:9:

```
ATG GCT CAG GCC ATG TTT TTT AAA GAA ATA GAA AAC CTA AAG GAA TAT        48
Met Ala Gln Ala Met Phe Phe Lys Glu Ile Glu Asn Leu Lys Glu Tyr
 1               5                  10                  15

TTT AAT GCA AGT AAT CCA GAT GTA TCG GAC GGT GGG TCT CTT TTC GTA        96
Phe Asn Ala Ser Asn Pro Asp Val Ser Asp Gly Gly Ser Leu Phe Val
                20                  25                  30

GAT ATT TTG AAG AAA TGG AGA GAG GAG AGT GAC AAA ACA ATC ATT CAG       144
Asp Ile Leu Lys Lys Trp Arg Glu Glu Ser Asp Lys Thr Ile Ile Gln
             35                  40                  45

AGC CAA ATT GTC TCT TTC TAC TTG AAA CTG TTT GAC AAC TTT AAA GAT       192
Ser Gln Ile Val Ser Phe Tyr Leu Lys Leu Phe Asp Asn Phe Lys Asp
 50                  55                  60

AAC CAG ATC ATT CAA AGG AGC ATG GAT ACC ATC AAG GAA GAC ATG CTT       240
Asn Gln Ile Ile Gln Arg Ser Met Asp Thr Ile Lys Glu Asp Met Leu
 65                  70                  75                  80

GCC AAG TTC TTA AAT AGC AGC ACC AGT AAG AGG GAG GAC TTC CTT AAG       288
Ala Lys Phe Leu Asn Ser Ser Thr Ser Lys Arg Glu Asp Phe Leu Lys
                 85                  90                  95

CTG ATT CAA ATT CCT GTC AAC GAT CTG CAG GTC CAG CGC AAG GCG ATA       336
Leu Ile Gln Ile Pro Val Asn Asp Leu Gln Val Gln Arg Lys Ala Ile
            100                 105                 110

AAT GAA CTC ATC AAA GTG ATG AAT GAT CTC TCA CCA AGA TCC AAC CTA       384
Asn Glu Leu Ile Lys Val Met Asn Asp Leu Ser Pro Arg Ser Asn Leu
        115                 120                 125

AGG AAG CGG AAA AGG AGT CAG AAT CTG TTT CGA GGC CGC AGA GCA TCG       432
Arg Lys Arg Lys Arg Ser Gln Asn Leu Phe Arg Gly Arg Arg Ala Ser
    130                 135                 140

AAA                                                                   435
Lys
145
```

(2) INFORMATION FOR SEQ ID NO:10:

(i) SEQUENCE CHARACTERISTICS:
        (A) LENGTH: 145 amino acids
        (B) TYPE: amino acid
        (D) TOPOLOGY: linear (ii) MOLECULE TYPE: protein (xi) SEQUENCE DESCRIPTION: SEQ ID NO:10:

```
Met Ala Gln Ala Met Phe Phe Lys Glu Ile Glu Asn Leu Lys Glu Tyr
 1               5                  10                  15

Phe Asn Ala Ser Asn Pro Asp Val Ser Asp Gly Gly Ser Leu Phe Val
                20                  25                  30
```

```
Asp Ile Leu Lys Lys Trp Arg Glu Glu Ser Asp Lys Thr Ile Ile Gln
        35                  40                  45

Ser Gln Ile Val Ser Phe Tyr Leu Lys Leu Phe Asp Asn Phe Lys Asp
    50                  55                  60

Asn Gln Ile Ile Gln Arg Ser Met Asp Thr Ile Lys Glu Asp Met Leu
65                  70                  75                  80

Ala Lys Phe Leu Asn Ser Ser Thr Ser Lys Arg Glu Asp Phe Leu Lys
                85                  90                  95

Leu Ile Gln Ile Pro Val Asn Asp Leu Gln Val Gln Arg Lys Ala Ile
                100                 105                 110

Asn Glu Leu Ile Lys Val Met Asn Asp Leu Ser Pro Arg Ser Asn Leu
            115                 120                 125

Arg Lys Arg Lys Arg Ser Gln Asn Leu Phe Arg Gly Arg Arg Ala Ser
    130                 135                 140

Lys
145

(2) INFORMATION FOR SEQ ID NO:11:

(i) SEQUENCE CHARACTERISTICS:
        (A) LENGTH: 432 base pairs
        (B) TYPE: nucleic acid
        (C) STRANDEDNESS: Not Relevant
        (D) TOPOLOGY: Not Relevant (ii) MOLECULE TYPE: cDNA (iii) HYPOTHETICAL: NO (ix) FEATURE:
        (A) NAME/KEY: mat_peptide
        (B) LOCATION: 1..432

(ix) FEATURE:
        (A) NAME/KEY: CDS
        (B) LOCATION: 1..432

(xi) SEQUENCE DESCRIPTION: SEQ ID NO:11:

ATG CAG GCC ATG TTT TTT AAA GAA ATA GAA AAC CTA AAG GAA TAT TTT      48
Met Gln Ala Met Phe Phe Lys Glu Ile Glu Asn Leu Lys Glu Tyr Phe
1               5                   10                  15

AAT GCA AGT AAT CCA GAT GTA TCG GAC GGT GGG TCT CTT TTC GTA GAT      96
Asn Ala Ser Asn Pro Asp Val Ser Asp Gly Gly Ser Leu Phe Val Asp
            20                  25                  30

ATT TTG AAG AAA TGG AGA GAG GAG AGT GAC AAA ACA ATC ATT CAG AGC     144
Ile Leu Lys Lys Trp Arg Glu Glu Ser Asp Lys Thr Ile Ile Gln Ser
        35                  40                  45

CAA ATT GTC TCT TTC TAC TTG AAA CTG TTT GAC AAC TTT AAA GAT AAC     192
Gln Ile Val Ser Phe Tyr Leu Lys Leu Phe Asp Asn Phe Lys Asp Asn
    50                  55                  60

CAG ATC ATT CAA AGG AGC ATG GAT ACC ATC AAG GAA GAC ATG CTT GGC     240
Gln Ile Ile Gln Arg Ser Met Asp Thr Ile Lys Glu Asp Met Leu Gly
65                  70                  75                  80

AAG TTC TTA AAT AGC AGC ACC AGT AAG AGG GAG GAC TTC CTT AAG CTG     288
Lys Phe Leu Asn Ser Ser Thr Ser Lys Arg Glu Asp Phe Leu Lys Leu
                85                  90                  95

ATT CAA ATT CCT GTC AAC GAT CTG CAG GTC CAG CGC AAG GCG ATA AAT     336
Ile Gln Ile Pro Val Asn Asp Leu Gln Val Gln Arg Lys Ala Ile Asn
                100                 105                 110

GAA CTC ATC AAA GTG ATG AAT GAT CTC TCA CCA AGA TCC AAC CTA AGG     384
Glu Leu Ile Lys Val Met Asn Asp Leu Ser Pro Arg Ser Asn Leu Arg
            115                 120                 125
```

```
AAG CGG AAA AGG AGT CAG AAT CTG TTT CGA GGC CGC AGA GCA TCG AAA        432
Lys Arg Lys Arg Ser Gln Asn Leu Phe Arg Gly Arg Arg Ala Ser Lys
    130                 135                 140
```

(2) INFORMATION FOR SEQ ID NO:12:

(i) SEQUENCE CHARACTERISTICS:
        (A) LENGTH: 144 amino acids
        (B) TYPE: amino acid
        (D) TOPOLOGY: linear (ii) MOLECULE TYPE: protein (xi) SEQUENCE DESCRIPTION: SEQ ID NO:12:

```
Met Gln Ala Met Phe Phe Lys Glu Ile Glu Asn Leu Lys Glu Tyr Phe
 1               5                  10                  15

Asn Ala Ser Asn Pro Asp Val Ser Asp Gly Gly Ser Leu Phe Val Asp
            20                  25                  30

Ile Leu Lys Lys Trp Arg Glu Glu Ser Asp Lys Thr Ile Ile Gln Ser
            35                  40                  45

Gln Ile Val Ser Phe Tyr Leu Lys Leu Phe Asp Asn Phe Lys Asp Asn
        50                  55                  60

Gln Ile Ile Gln Arg Ser Met Asp Thr Ile Lys Glu Asp Met Leu Gly
65                  70                  75                  80

Lys Phe Leu Asn Ser Ser Thr Ser Lys Arg Glu Asp Phe Leu Lys Leu
                85                  90                  95

Ile Gln Ile Pro Val Asn Asp Leu Gln Val Gln Arg Lys Ala Ile Asn
               100                 105                 110

Glu Leu Ile Lys Val Met Asn Asp Leu Ser Pro Arg Ser Asn Leu Arg
           115                 120                 125

Lys Arg Lys Arg Ser Gln Asn Leu Phe Arg Gly Arg Arg Ala Ser Lys
    130                 135                 140
```

USE OF CANINE INTERFERON-γ(IFN-γ) TO TREAT NON-ATOPIC DERMATITIS

TECHNICAL FIELD

The present invention relates to a therapeutic agent, composed of canine interferon-γ and a treatment for canine intractable dermatitis using the agent.

BACKGROUND ART

Interferon-γ (hereinafter interferon is referred to as "IFN") is mainly produced by T-cells and is known to have three main functions, i.e., antiviral activity, anti-cell proliferation activity, and immunoregulation (reference 1). With the recent development in gene manipulation techniques, not only human IFN genes but also animal IFN genes, such as bovine, equine, and feline IFN genes have been isolated. Concerning canines, IFN-α, β, and γ have been reported (references 2 and 3). Compared with human or mouse IFN-γ, however, only a little knowledge has been obtained from in vitro and in vivo studies on canine IFN-γ, and there is no report using canine IFN-γ as a therapeutic agent for any particular canine disease.

In humans, IFN-γ has already been put into practical use as a therapeutic agent for malignant tumors. Concerning skin diseases, Hanifin et al. (reference 4) and Rheinhold et al. (references 5 and 6) reported its effectiveness for treating atopic dermatitis and steroid dependent asthma. There is doubt (reference 7), however, regarding the use of human IFN-γ for human atopic dermatitis because of the following reasons: for effectively treating human atopic dermatitis with human IFN-γ, daily administration for 6 consecutive weeks or more is necessary; IFN-γ has adverse effects such as fever and headache and gives the patients a rather large amount of stress while its effects are rather small; and IFN-γ formulations are expensive.

Concerning human dermatitis, diagnosis criteria have been established (reference 8) and a genetic background is regarded as being an important criterion. In addition, human atopic dermatitis is known to be a type I allergic reaction, in which production of an excess amount of IgE in response to foods, animal scales, insect poisons, and the like is an important component (reference 9). However, there have not been any systematic studies done on canine atopic dermatitis. Therefore, the evaluation criteria are unclear and the relationship between the production of excess canine IgE and atopic dermatitis is not clear.

In general, canine skin diseases include eczema, urticaria, allergic dermatitis, traumatic dermatitis, mange, otitis externa, pruritic dermatitis, and the like. The following agents are conventionally used for the above diseases: antihistamines (diphenhydramines), antiphlogistics (dibucaine hydrochloride, etc.), insecticides, and bacteriocides (malathion, benzalkonium chloride, etc.), and steroids (dexamethasone, etc.).

Among therapeutic agents of the prior art used for treating canine skin diseases, however, there are disadvantages in the use of non-steroidal agents as their therapeutic effects are very low. Although steroidal agents have extremely strong pharmacological effects, they occasionally show adverse effects, such as enhancement of infection at disease regions and increases in vascular-wall fragility. Also, long-term administration of steroids may cause obesity or systematic adverse effects as a result of effects on other organs.

In general, canine skin diseases cannot be cured as well as those of humans because of inferior housing conditions. Thus dogs are frequently treated with repeated doses of the above therapeutic agents of the prior art. Treatment periods are thus extended, and occasionally, diseases are not completely cured even if treatment is continued for more than half a year. In some cases, treatment is extended for several years, resulting in great stress for the dog owner. Therefore, there is a demand for a therapeutic agent with a rapid and sustained effect on canine intractable dermatitis that cannot completely be cured by long-term treatment using therapeutic agents of the prior art.

Accordingly, an object of the present invention is to provide an effective therapeutic agent for canine intractable dermatitis.

DISCLOSURE OF THE INVENTION

Inventors of the present invention accomplished the present invention by finding that canine skin diseases, which could hardly be cured by formulations of the prior art, were remarkably improved by administering a canine IFN-γ formulation. In other words, the object of the present invention is to provide a therapeutic agent, containing canine IFN-γ as the active ingredient, for canine intractable dermatitis, and a method for treating canine intractable dermatitis using the therapeutic agent.

BEST MODE FOR CARRYING OUT THE INVENTION

For example, canine IFN-γ of the present invention is a polypeptide having an amino acid sequence shown as SEQ. ID. NO. 2, 4, 6, 8, 10, or 12: However, the present invention includes polypeptides which are within the spirit of the present invention, for example, even if the amino acid sequence has a replacement, insertion, or deletion of one or more amino acid residues, the polypeptide is included in the present invention as long as it shows biological activity of the original IFN-γ as is shown in reference 1. This is because in such a case the polypeptide is regarded as having the effect of the present invention.

Although canine IFN-γ may be produced by an isolation and purification process from natural biomaterials, by chemical synthesis, or by recombinant DNA techniques, the use of canine IFN-γ produced by recombinant DNA techniques is preferable from an economic point of view. The method for producing canine IFN-γ by recombinant DNA techniques is not particularly limited. For example, canine IFN-γ can be produced by using host cells or host animals into which a gene, coding for the whole or part of an amino acid sequence of canine IFN-γ shown in SEQ. ID. NOs. 1 to 6, has been transduced by an already established conventional method. For example, after proliferating *Escherichia coli*, into which cDNA of the whole or part of a base sequence of canine IFN-γ shown in SEQ. ID. NO. 1, 3, 5, 7, 9, or 11 has been transduced, canine IFN-γ can be obtained from the bacterial cells or supernatants of the bacterial cultures by isolation and purification. Furthermore, after infecting cells of a cultured insect cell line such as *Spondoptera frugiperda* or *bombyx mori* or silk worms with Baculovirus, into which cDNA of the whole or part of the base sequence of canine IFN-γ shown in SEQ. ID. NOs. 1 to 6 has been transduced, canine IFN-γ can be obtained by purification from the cultured cells, supernatants of cell cultures, or hemolymph of silk worms. In the above cases, the base sequence of canine IFN-γ is not limited to that of SEQ ID NOs. 1, 3, 5, 7, 9, or 11, as long as it is translated into the amino acid sequence of SEQ. ID. NOs. 2, 4, 6, 8, 10, or 12. In addition, canine IFN-γ having similar effects to the present invention can be produced by using cDNA having a base sequence coding for a poypeptide which is included in the spirit of the present invention, even if the amino acid sequence has a replacement, insertion, or deletion of one or more amino acid residues.

The method for isolating and purifying canine IFN-γ produced by recombinant DNA techniques is not particularly limited, and conventional protein purification methods can be employed. For example, with the antiviral activity of canine IFN-γ as an index, canine IFN-γ can be purified and isolated by combining the following methods for desalting or concentration: chromatography employing silica gel carriers, ion exchange carriers, gel filtration carriers, chelate carriers, pigment ligand carriers, or the like; ultrafiltration; gel filtration; dialysis; salting out; and the like. In the above procedure, the antiviral activity of canine IFN-γ can be measured according to the CPE method of reference 10 using vesicular stomatitis virus (VSV) as the virus and canine MDCK cells (ATCC CCL-34) as the sensitive cells.

In the present invention, canine intractable dermatitis is defined as a group of skin diseases which are not remarkably improved by treatment with therapeutic agents for canine skin diseases of the prior art for at least half a year, or which recur after the symptoms had once been reduced. Examples of the therapeutic agents for treating canine skin disease of the prior art are as follows: exodermatic bacteriocidic disinfectants, antihistamines, steroid hormones, analgesics, antipruritics, astringents, anti-inflammatory agents, and agents for parasitic skin diseases. Frequently, canine intractable dermatitis is not remarkably improved by steroid hormones, or even if the symptoms are reduced, they recur soon after discontinuing the administration. Canine intractable dermatitis includes allergic dermatitis, pemphigus, hypertrophic dermatitis, mycodermatitis, atopic dermatitis, intractable drug eruption, and the like.

In addition to canine IFN-γ, a therapeutic agent for canine intractable dermatitis used in the present invention may optionally contain other components. Components added to the agent are mainly determined by the route of administration. When the agent is used as a solid, for example, fillers such as lactose, binders such as carboxymethyl cellulose and gelatin, coloring agents, and coating agents may be employed; such an agent that is in a solid form may be suitable for oral administration. In addition, the agent can be a formulation which is applied externally to the lesions, such as a cream, a lotion, a latex, and the like, by adding carriers or excipients, such as white petrolatum, cellulose derivatives, surfactants, polyethylene glycol, silicone, or olive oil. When the agent is administered as a liquid, it may contain generally used physiologically acceptable solvents, emulsifiers, and stabilizers. Examples of solvents are water, phosphate buffered saline (PBS), and isotonic physiological saline; examples of emulsifiers are polyoxyethylene surfactants, fatty acid surfactants, and silicone. Examples of stabilizers are proteins, such as canine serum albumin and gelatin, polyols, such as polyethylene glycol and ethylene glycol, and saccharides, such as sorbitol and trehalose. Although the administration route of the therapeutic agent of the present invention is not particularly limited, stronger therapeutic effects can be expected by injection. Any injection method including intravenous administration, intramuscular administration, subcutaneous administration, intraperitoneal administration, and intrapleural administration can be employed, however subcutaneous administration is preferable because it is a simple procedure and causes a lower amount of stress to the patient dogs.

Although the treatment dose is appropriately determined according to the size of the individual, the route of administration, the symptoms, and the like, a dosage sufficient for reducing the symptoms of canine intractable dermatitis is generally administered. For example, administration of 0.002 to 1.0 MU/kg of canine IFN-γ per day provides sufficient effects. Preferably, from an economic and effectiveness point of view, 0.005 to 0.5 MU/kg per day is administered. In the above, kg is the unit of the patient dog weight and U is the unit number determined by the antiviral activity of IFN-γ measured according to the CPE method of reference 10 using vesicular stomatitis virus (VSV) as the virus and canine MDCK cells, (ATCC CCL-34) as the sensitive cells. The amount of IFN-γ that decreases the cytopathic effect of VSV against canine MDCK cells (ATCC CCL-34) by 50% is defined as one unit.

In addition, the frequency of administration is also determined by the individual, the route of administration, the symptoms, and the like. However, it is generally thought that by administration once or twice a week, the symptoms are remarkably reduced at the second week after the beginning of the treatment. Although it is possible to alter the frequency or number of administrations while observing the treatment course, administration twice to ten times every other day or seven days is preferable from the point of view of the amount of stress to the dog owners and the therapeutic effect.

In the method for treatment of the invention, a therapeutic agent of the prior art for treating canine skin diseases can be adjuvantly used in combination. In such a case, the therapeutic agents of the present invention are administered with other agents selected from antihistamines (diphenhydramines), antiphlogistics (dibucaine hydrochloride, etc.), insecticides and bateriocides (malathion, benzalkonium chloride, etc.), steroids (dexamethasone, etc.), and the like.

As is above-mentioned in detail, the present invention provides a therapeutic agent for canine intractable dermatitis having canine IFN-γ as the active ingredient and a treatment method. According to the therapeutic agent and treatment method of the present invention, canine skin diseases which are hardly cured by therapeutic agents for canine dermatitis of the prior art can be treated effectively without adverse effects.

EXAMPLES

The present invention is illustrated in more detail with reference to the following examples, though the present invention is not limited to these examples.

Example 1

Measurement of Antiviral Activity of Canine IFN-γ

Basically, antiviral activity of canine IFN-γ measured according to the method described in reference 10 using canine MDCK (ATCC CCL-34) cells and VSV. Briefly, a diluted solution of a sample containing canine IFN-γ was added to the canine MDCK (ATCC CCL-34) cells, which had been cultured on a 96-well microplate at 37° C. until they reached a confluent state. Then the cells were further incubated at 37° C. for 20 to 24 hours to induce antiviral activity. The cells were mixed with VSV and cultured for 24 hours at 37° C. The living canine MDCK cells that adhered to the microplate were stained with a crystal violet solution containing 20% formalin. The amount of crystal violet on the microplate was determined by measuring the absorbance at 570 nm so as to evaluate the amount of canine IFN-γ at which 50% of the cells were alive. The thus-obtained amount of canine IFN-γ was defined as one unit (1 U) of antiviral activity.

Example 2

Canine IFN-γ Production by *Escherichia coli* Harboring DNA Coding for Canine IFN-γ

In accordance with a conventional method, cDNA of canine IFN-γ having the nucleotide sequence of SEQ. ID. NO. 5 was inserted in pET8c, which is an expression vector for *Escherichia coli*. Then *Escherichia coli* HB101 were transformed by a conventional method. The thus-obtained transformants were inoculated into LB medium containing 100 ug/ml of ampicillin. The transformants were cultured at 37° C. until the $OD_{600}$ reached approximately 0.7. Isopropyl-β-D-thiogalactopyranoside (IPTG) was added to a final concentration of 0.5 mM, and then, the cells were cultured for an additional 1.5 hours. The thus-obtained 11 L of culture medium was centrifuged at 12,000 rpm for 5 min. to separate the supernatant, the residue was suspended in 60 ml of 10 mM tris-Cl (pH 7.5), and the bacterial cells were completely disrupted by sonication on ice. The resultant was centrifuged at 20,000 rpm for 30 min. and the supernatant was recovered to obtain 54 ml of a soluble protein fraction. This fraction had at least $10^6$ U/ml of antiviral activity.

Example 3

Canine IFN-γ Production by *Bombyx mori* Cells or Silk Worms Harboring DNA Coding for Canine IFN-γ

In accordance with a conventional method, cDNA of canine IFN-γ having the nucleotide sequence of SEQ. ID. NO. 1 was transduced into a vector pBM030 (reference 11) to obtain a recombinant plasmid pBMγ. Recombinant Baculoviruses were prepared in accordance with the method of reference 11. Briefly, DNA of both *Bombyx mori* nuclear polyhedrosis virus BmNPV T3 strain (reference 11) and of the recombinant plasmid pBMγ were co-transfected into *Bombyx mori* cells (Bm-N cells) by a calcium phosphate method. Then, recombinant Baculovirus rBNVγ comprising DNA coding for canine IFN-γ was cloned by the limiting dilution method with the following fact as an index: microscopically, when viral infection was observed and when polyhedrin particles were not being formed. Each 0.5 ml of the thus-obtained recombinant virus solution was added to approximately $3 \times 10^6$ Bm-N cells cultured in a TC-100 medium containing 10% FBS in a 25 $cm^2$-tissue culture flask. After 30 min., the medium was replaced with 5 ml of fresh TC-100 medium containing 10% fetal bovine serum (FBS) and cultured at 27° C. for 3 days. The supernatant of the medium was collected by centrifugation and found to have an antiviral activity of $10^4$ U/ml.

Silk worms in the second day of their fifth instar were injected with 50 ul/worm of the liquid of the recombinant Baculovirus rBNVγ comprising DNA coding for canine IFN-γ, fed a commercially available artificial feed (Kanebo Silk Elegance Co.) at 25° C. for 4 days, then the abdomen of ten of these silk worms was cut open to collect their hemolymph into an Eppendorf tube cooled on ice. The resulting hemolymph was centrifuged, and the thus-obtained supernatant was sterilized by filtration using a 0.22 um filter. The resulting supernatant had a measured antiviral activity of $10^7$ U/ml.

Example 4

Preparation of Canine IFN-γ

A 20 mM phosphate buffer (pH 7.0), was used to obtain a two-fold dilution of 50 ml of the soluble protein fraction obtained in EXAMPLE 2. The diluted protein fraction was added to a column packed with 20 ml of silica gel which was equilibrated with the same buffer; the column was washed with a sufficient amount of 20 mM phosphate buffer (pH 7.0). The absorbed components were eluted with 20 mM phosphate buffer (pH 7.0) containing 3 M ammonium chloride and 5% polyethylene glycol to collect a 45 ml eluate. The thus-obtained eluate contained approximately 30 mg of protein and the yield of protein was approximately 30%. After dialyzing 40 ml of the eluate twice with a 10-times volume of 20 mM phosphate buffer (pH 7.0), the resultant was added to a column packed with 10 ml of SP SEPHAROSE™ FF and the column was washed with 100 ml of 20 mM phosphate buffer (pH 7.0). The absorbed components were eluted by a NaCl concentration gradient to collect eluted fractions containing canine IFN-γ. The thus-obtained eluate fraction contained approximately 15 mg of protein and the purity of the canine IFN-γ was approximately 30%. The eluate was similarly re-chromatographed and the eluate following re-chromatography was desalted by a conventional method using a gel filtration column packed with 80 ml of SEPHADEX™ G-25 to obtain 10 ml of a purified canine IFN-γ fraction. Analysis using SDS-polyacrylamide gel electrophoresis showed that this fraction contained 5 mg of protein and the purity of the canine IFN-γ was at least 80%.

About 2 mg of canine IFN-γ having more than 85% purity was obtained from 100 ml of silkworm hemolymph obtained in Example 3, in which recombinant Baculoviruses were inactivated.

Example 5

Production of a Canine IFN-γ Formulation

A physiological saline for injection, low-molecular gelatin for injection (Nitta Gelatin Inc.), and sorbitol were added to the purified canine IFN-γ solution obtained in EXAMPLE 4 to make a final gelatin concentration of 30%. The resultant was then treated with POSIDYNE (Poll Filtron Co.) to remove pyrogens, and 1 ml per vial of filtrate was added to glass vials sterilized by dry heat at 250° C. for 2 hours. A canine IFN-γ formulation, with each vial containing 0.1 MU to 2.5 MU of canine IFN-γ, was then obtained by lyophilizing aseptically. This canine IFN-γ formulation was stable in the dark at room temperature and highly soluble in water or physiological saline.

Example 6

Treatment of Canine Intractable Dermatitis by Canine IFN-γ

Dogs that had been treated for 0.5 to 7 years with therapeutic agents of the prior art without showing a remarkable reduction in symptoms of skin diseases or exhibiting repeated recurrences were employed for this study. The subjects of this study included those that had the complication of mycosis supposedly due to adverse effects from steroid hormones. The canine IFN-γ formulation prepared in EXAMPLE 5 was dissolved in 1 ml of physiological saline for injection and administered subcutaneously to the subjects; the therapeutic effects were evaluated by observing the clinical symptoms of skin diseases and adverse effects. Table 1 shows the dose per administration and administration schedule. The severity of canine skin diseases was evaluated as follows: 6 parameters, i.e., erythema, papule, eczema, lichen excoriation, and scale, were scored as 0 (none), 1 (weak), 2 (moderate), and 3 (severe). The total scores of the parameters were defined as the total clinical severity. The therapeutic effects were evaluated from the severity of the clinical symptoms. The therapeutic effects obtained with the canine IFNY-γ formulation prepared from *Escherichia coli* are shown in Table 1. Table 3 shows the therapeutic effect obtained with the formulation of IFN-γ obtained from silk worms.

As is apparent from Tables 1 and 3, in each of the dogs employed for this study the clinical severity of the skin diseases was remarkably reduced, indicating that canine IFNY-γ is extremely effective in the treatment of skin diseases. In addition, the symptoms of the five dogs shown in Table 1 had not been notably reduced by steroid hormone therapy, or had recurred soon after discontinuing the administration of steroid hormones, which is thought to be the most effective among therapeutic agents of the prior art. However, the symptoms were rapidly cured by one or two administrations of canine IFN-γ of the present invention. Furthermore, there were no clinically meaningful adverse effects observed in any of the five dogs.

Example 7

Treatment of Canine Intractable Dermatitis by Canine IFN-γ in Combination with Other Therapeutic Agents Similarly to EXAMPLE 6, dogs that had been treated for at least half a year without showing remarkable reduction in symptoms of skin diseases by therapeutic agents of the prior art or presenting with repeated recurrences were employed for this study. Tests and therapeutic-effect evaluation were carried out according to methods similar to those described in EXAMPLE 6, except that the therapeutic agents shown in Table 2 were used in combination with the canine IFN-γ formulation prepared in EXAMPLE 5. The results in Table 2 show that canine IFN-γ rapidly reduces the clinical symptoms due to canine intractable dermatitis and is effective even when it is used in combination with therapeutic agents of the prior art. In addition, there is a trend that canine IFN-γ exhibits sufficient therapeutic effects at small dose as compared with EXAMPLE 6 when it is used in combination with therapeutic agents of the prior art. Furthermore, adverse effects because of the combined therapy are not particularly observed.

TABLE 1

Therapeutic effects of dog IFN-γ on dog intractable dermatitis (dog IFN-γ alone)

| Test dog No. | Day of administration 1) | Dose of dog IFN-γ (MU/kg) | Erythema | Papule | Eczema | Lichen | Excoriation | Scale | Total clinical severity | Evaluation |
|---|---|---|---|---|---|---|---|---|---|---|
| 1 | 0 | 0.400 | 3 | 3 | 2 | 2 | 1 | 1 | 12 | Very |
|   | 3 | 0.400 | 3 | 1 | 1 | 0 | 1 | 1 | 7 | effective |
|   | 7 | 0.400 | 1 | 0 | 1 | 0 | 1 | 1 | 4 | |
|   | 10 | 0.400 | 0 | 0 | 1 | 0 | 0 | 0 | 1 | |
|   | 14 | 0.400 | 0 | 0 | 0 | 0 | 0 | 0 | 0 | |
|   | 22 | 0.400 | 0 | 0 | 0 | 0 | 0 | 0 | 0 | |
| 2 | 0 | 0.007 | 3 | 3 | 2 | 1 | 2 | 2 | 13 | Very |
|   | 7 | 0.007 | 1 | 1 | 1 | 1 | 1 | 1 | 6 | effective |
|   | 16 | 0.007 | 0 | 0 | 0 | 0 | 0 | 0 | 0 | |
| 3 | 0 | 0.003 | 3 | 2 | 2 | 2 | 1 | 1 | 11 | Effective |
|   | 4 | 0.003 | 2 | 2 | 1 | 1 | 0 | 0 | 6 | |
|   | 8 | 0.003 | 2 | 1 | 1 | 1 | 0 | 0 | 5 | |
|   | 11 | 0.003 | 1 | 1 | 1 | 0 | 0 | 0 | 3 | |
|   | 17 | 0.003 | 1 | 1 | 0 | 1 | 0 | 0 | 3 | |
| 4 | 0 | 0.008 | 3 | 2 | 3 | 2 | 2 | 1 | 13 | Effective |
|   | 7 | 0.030 | 2 | 2 | 1 | 2 | 2 | 1 | 10 | |
|   | 19 | 0.016 | 2 | 2 | 1 | 1 | 1 | 1 | 8 | |
|   | 27 | 0.008 | 1 | 1 | 0 | 1 | 0 | 1 | 4 | |
|   | 34 | 0.004 | 1 | 1 | 0 | 1 | 0 | 1 | 4 | |
| 5 | 0 | 0.007 | 3 | 3 | 2 | 1 | 2 | 1 | 12 | Effective |

TABLE 1-continued

Therapeutic effects of dog IFN-γ on dog intractable dermatitis (dog IFN-γ alone)

| Test dog No. | Day of administration 1) | Dose of dog IFN-γ (MU/kg) | Erythema | Papule | Eczema | Lichen | Excoriation | Scale | Total clinical severity | Evaluation |
|---|---|---|---|---|---|---|---|---|---|---|
| | 8 | 0.004 | 3 | 3 | 1 | 1 | 2 | 1 | 11 | |
| | 15 | 0.004 | 1 | 1 | 1 | 0 | 1 | 0 | 4 | |

Severity of clinical symptoms 2)

1) Day of administration: defined such that the initial day of administration is day 0.
2) Severity of clinical symptoms: 0 (none), 1 (weak), 2 (moderate), and 3 (severe).

TABLE 2

Therapeutic effects of dog IFN-γ on dog intractable dermatitis (combination with conventional therapeutic agent(s))

| Test dog No. | Day of administration 1) | Dose of dog IFN-γ (MU/kg) | Erythema | Papule | Eczema | Lichen | Excoriation | Scale | Total clinical severity | Evaluation | Combined agent(s) |
|---|---|---|---|---|---|---|---|---|---|---|---|
| 6 | 0 | 0.100 | 3 | 2 | 2 | 1 | 2 | 1 | 11 | Effective | Predonine (4 mg/dog) |
| | 3 | 0.100 | 2 | 1 | 1 | 1 | 1 | 1 | 7 | | None |
| | 7 | 0.100 | 1 | 1 | 1 | 1 | 0 | 0 | 4 | | None |
| | 12 | 0.100 | 1 | 0 | 0 | 1 | 0 | 0 | 2 | | None |
| 7 | 0 | 0.040 | 2 | 3 | 2 | 2 | 1 | 1 | 11 | Very effective | Predonine (4 mg/dog), Lincomycin (50 mg/dog) |
| | 3 | 0.040 | 1 | 2 | 1 | 1 | 1 | 0 | 6 | | None |
| | 5 | 0.040 | 0 | 0 | 0 | 0 | 0 | 0 | 0 | | None |
| 8 | 0 | 0.007 | 3 | 3 | 2 | 1 | 2 | 1 | 12 | Very effective | Predonine (2.5 mg/dog) |
| | 6 | 0.007 | 3 | 2 | 1 | 0 | 1 | 0 | 7 | | None |
| | 11 | 0.007 | 0 | 1 | 1 | 0 | 1 | 0 | 3 | | None |
| | 19 | 0.007 | 0 | 0 | 0 | 0 | 1 | 0 | 1 | | Predonine (2.5 mg/dog) |
| | 23 | 0.004 | 0 | 0 | 0 | 0 | 0 | 0 | 0 | | None |
| 9 | 0 | 0.010 | 3 | 2 | 2 | 1 | 2 | 1 | 11 | Effective | Predonine (4 mg/dog), Lincomycin (50 mg/dog) |
| | 3 | 0.010 | 3 | 2 | 1 | 1 | 1 | 0 | 8 | | None |
| | 7 | 0.010 | 2 | 1 | 1 | 0 | 0 | 0 | 4 | | None |
| | 11 | 0.005 | 1 | 1 | 1 | 0 | 1 | 0 | 4 | | None |
| | 19 | 0.002 | 1 | 0 | 1 | 0 | 1 | 0 | 3 | | Predonine (2.5 mg/dog) |
| | 27 | 0.002 | 0 | 1 | 0 | 0 | 1 | 0 | 2 | | Predonine (2.5 mg/dog) |
| 10 | 0 | 0.010 | 3 | 1 | 2 | 2 | 1 | 1 | 10 | Effective | Predonine (10 mg/dog) |
| | 11 | 0.010 | 1 | 1 | 2 | 1 | 1 | 1 | 7 | | Predonine (1 mg/dog) |
| | 18 | 0.010 | 0 | 1 | 1 | 0 | 1 | 0 | 3 | | None |
| 11 | 0 | 0.020 | 3 | 3 | 2 | 3 | 1 | 1 | 13 | Effective | Predonine (1.25 mg/dog) |
| | 6 | 0.020 | 2 | 2 | 1 | 2 | 1 | 0 | 8 | | None |
| | 14 | 0.020 | 2 | 2 | 1 | 1 | 0 | 0 | 6 | | None |
| | 21 | 0.020 | 1 | 1 | 0 | 1 | 0 | 0 | 3 | | None |
| | 28 | 0.020 | 0 | 1 | 0 | 1 | 0 | 0 | 2 | | None |

1) Day of administration: defined such that the initial day of administration is day 0.
2) Severity of clinical symptoms: 0 (none), 1 (weak), 2 (moderate), and 3 (severe).

TABLE 3(1)

Therapeutic effects of dog IFN-γ on dog intractable dermatitis (dog IFN-γ alone)

| Test dog No. | Disease | Day of administration 1) | Dose of dog IFN-γ (MU/Kg) | Erythema | Papule | Eczema | Lichen | Excoriation | Scale | Total clinical severity | Evaluation |
|---|---|---|---|---|---|---|---|---|---|---|---|
| 12 | Atopic dermatosis | 0 | 0.030 | 3 | 2 | 3 | 0 | 2 | 0 | 10 | Very effective |
| | | 5 | 0.030 | — | — | — | — | — | — | — | |

TABLE 3(1)-continued

Therapeutic effects of dog IFN-γ on dog intractable dermatitis (dog IFN-γ alone)

| Test dog No. | Disease | Day of administration 1) | Dose of dog IFN-γ (MU/Kg) | Erythema | Papule | Eczema | Lichen | Excoriation | Scale | Total clinical severity | Evaluation |
|---|---|---|---|---|---|---|---|---|---|---|---|
| | | 12 | 0.030 | — | — | — | — | — | — | — | |
| | | 16 | 0.030 | — | — | — | — | — | — | — | |
| | | 23 | 0.030 | — | — | — | — | — | — | — | |
| | | 26 | 0.030 | 1 | 1 | 0 | 0 | 0 | 0 | 2 | |
| 13 | Atopic dermatosis | 0 | 0.01 | 2 | 2 | 2 | 0 | 0 | 0 | 6 | Very effective |
| | | 8 | 0.01 | — | — | — | — | — | — | — | |
| | | 14 | 0.01 | — | — | — | — | — | — | — | |
| | | 21 | 0.01 | 0 | 0 | 0 | 0 | 0 | 0 | 0 | |
| 14 | Atopic dermatosis | 0 | 0.002 | 3 | 2 | 2 | 0 | 1 | 0 | 8 | Effective |
| | | 3 | 0.002 | — | — | — | — | — | — | — | |
| | | 6 | 0.002 | — | — | — | — | — | — | — | |
| | | 10 | 0.002 | — | — | — | — | — | — | — | |
| | | 13 | 0.002 | 1 | 0 | 0 | 0 | 0 | 0 | 1 | |
| 15 | Atopic dermatosis | 0 | 0.004 | 3 | 2 | 3 | 0 | 0 | 0 | 8 | Effective |
| | | 3 | 0.004 | — | — | — | — | — | — | — | |
| | | 7 | 0.004 | — | — | — | — | — | — | — | |
| | | 9 | 0.004 | — | — | — | — | — | — | — | |
| | | 19 | 0.004 | 1 | 1 | 0 | 1 | 0 | 0 | 3 | |
| 16 | Pemphigus | 0 | 0.01 | 3 | 3 | 3 | 3 | 3 | 0 | 15 | Effective |
| | | 3 | 0.01 | — | — | — | — | — | — | — | |
| | | 7 | 0.01 | — | — | — | — | — | — | — | |
| | | 10 | 0.01 | — | — | — | — | — | — | — | |
| | | 15 | 0.01 | — | — | — | — | — | — | — | |
| | | 20 | 0.01 | 1 | 1 | 1 | 1 | 1 | 0 | 5 | |

1) Day of administration: defined such that the initial day of administration is day 0.
2) Severity of clinical symptoms: 0 (none), 1 (weak), 2 (moderate), and 3 (severe).

TABLE 3(2)

Therapeutic effects of dog IFN-γ on dog intractable dermatitis (dog IFN-γ alone)

| Test dog No. | Disease | Day of administration 1) | Dose of dog IFN-γ (MU/Kg) | Erythema | Papule | Eczema | Lichen | Excoriation | Scale | Total clinical severity | Evaluation |
|---|---|---|---|---|---|---|---|---|---|---|---|
| 17 | Acanthosis | 0 | 0.010 | 3 | 3 | 3 | 3 | 3 | 3 | 18 | Effective |
| | | 4 | 0.010 | — | — | — | — | — | — | — | |
| | | 7 | 0.010 | — | — | — | — | — | — | — | |
| | | 12 | 0.010 | — | — | — | — | — | — | — | |
| | | 15 | 0.010 | — | — | — | — | — | — | — | |
| | | 19 | 0.010 | 2 | 2 | 2 | 2 | 2 | 2 | 12 | |
| 18 | Chronic dermatosis/ ulcerative dermatosis | 0 | 0.005 | 3 | 3 | 3 | 3 | 3 | 3 | 18 | Very effective |
| | | 3 | 0.005 | — | — | — | — | — | — | — | |
| | | 7 | 0.005 | — | — | — | — | — | — | — | |
| | | 11 | 0.005 | — | — | — | — | — | — | — | |
| | | 15 | 0.005 | — | — | — | — | — | — | — | |
| | | 18 | 0.005 | 0 | 1 | 1 | 0 | 0 | 0 | 2 | |
| 19 | Chronic eczema | 0 | 0.002 | 3 | 2 | 2 | 0 | 1 | 0 | 8 | Effective |
| | | 12 | 0.002 | — | — | — | — | — | — | — | |
| | | 17 | 0.002 | 1 | 1 | 1 | 0 | 0 | 0 | 3 | |
| 20 | Chronic eczema | 0 | 0.002 | 2 | 2 | 2 | 0 | 0 | 2 | 8 | Very effective |
| | | 8 | 0.002 | — | — | — | — | — | — | — | |
| | | 13 | 0.002 | — | — | — | — | — | — | — | |
| | | 9 | 0.002 | — | — | — | — | — | — | — | |
| | | 19 | 0.002 | 1 | 1 | 1 | 0 | 0 | 1 | 4 | |

1) Day of administration: defined such that the initial day of administration is day 0.
2) Severity of clinical symptoms: 0 (none), 1 (weak), 2 (moderate), and 3 (severe).

References Cited
1. Ijzermans et al.: Immunobiology, 179, 456–473 (1989)
2. Adolf et al.: J. Interferon-Research, 7, 173–183 (1987)
3. Devos et al.: J. Interferon-Research, 12, 95–102 (1992)
4. Hanifin et al.: J. Am. Acad. Dermatol., 28, 189–197 (1993)
5. Rheinhold et al.: Lancet, 335, 1282 (1990)
6. Rheinhold et al.: J. Am. Acad. Dermatol., 29, 58–63 (1993)
7. Nishioka et al.: J. Dermatol., 22, 181–185 (1995)
8. Williams: Br. J. Dermatol., 131, 397–405 (1994)

9. Sampson et al.: J. Allergy Clin. Immunol., 81, 635–645 (1988)
10. Nippon Seikagaku Gakkai (ed): Zoku-Seikagakujikkenkoza, 5, 250–256, Tokyo Kagakudojin (1986)
11. Horiuchi et al.: Agic. Biol. Chem., 51, 1573–1580, (1987)

---

What is claimed is:

1. A method for treating an intractable canine dermatitis other than atopic dermatitis, comprising the step of administering a therapeutic agent comprising canine interferon-γ to a dog suffering from said intractable dermatitis by injection.

2. A method for treating canine intractable dermatitis according to claim 1, wherein said therapeutic agent is injected subcutaneously.

3. A method for treating canine intractable dermatitis according to claim 1 or 2, wherein the administration dose of said therapeutic agent is 0.002 to 1.0 MU/kg body weight per administration.

4. A method for treating canine intractable dermatitis according to claim 1, wherein said canine intractable dermatitis is refractory to treatment with steroid hormones.

5. A method for treating canine intractable dermatitis according to claim 1, wherein said therapeutic agent for canine intractable dermatitis is administered at intervals of at least one day.

6. A method for treating canine intractable dermatitis as set forth in claim 1, wherein said therapeutic agent for canine intractable dermatitis is administered in combination with a steroid or an anti-allergic agent.

7. A method for treating intractable dermatitis as set forth in claim 1, wherein said canine interferon-γ is produced by a recombinant DNA technique.

8. A method for treating intractable dermatitis as set forth in claim 7, wherein said canine interferon-γ is produced by *Escherichia coli* cells, *Bombyx mori* cells, or silk worms, into which DNA coding for an amino acid sequence of canine interferon-γ has been transduced.

9. A method for treating intractable dermatitis as set forth in claim 1, wherein said canine therapeutic agent contains canine interferon-γ and a protein or a saccharide.

10. A method for treating an intractable canine dermatitis selected from the group consisting of allergic dermatitis other than atopic dermatitis, pemphigus, hypertrophic dermatitis, mycodermatitis and intractable drug eruption, comprising administering a therapeutic agent comprising canine interferon-γ to a dog suffering from said intractable dermatitis by injection.

11. A method for treating canine intractable dermatitis as set forth in claim 10, wherein said therapeutic agent is injected subcutaneously.

12. A method for treating canine intractable dermatitis as set forth in claim 10 or 11, wherein the dose of said therapeutic agent is from 0.002 to 1.0 MU/kg body weight per injection.

13. A method for treating canine intractable dermatitis as set forth in claim 10, wherein said therapeutic agent is administered at least one time per day.

14. A method for treating canine intractable dermatitis as set forth in claim 10, wherein said therapeutic agent is administered in combination with a steroid or anti-allergic agent.

15. A method for treating canine intractable dermatitis as set forth in claim 10, wherein said canine interferon gamma is a recombinant interferon gamma having the amino acid sequence set forth as residues 1 to 142 of SEQ. ID. NO.: 2, residues 1 to 142 of SEQ. ID. NO.: 4, residues 1 to 142 of SEQ. ID. NO.: 6, residues 1 to 142 of SEQ. ID. NO.: 8, or SEQ. ID. NO.: 10 or SEQ. ID. NO.: 12.

16. A method for treating canine intractable dermatitis as set forth in claim 15, wherein said recombinant interferon-γ is produced in an *Escherichia coli* or *Bombyx mori* cell or in a silk worm.

17. A method for treating canine intractable dermatitis as set forth in claim 10, wherein said therapeutic agent further comprises a protein or a saccharide.

* * * * *